United States Patent [19]

Sommer

[11] Patent Number: 4,647,198
[45] Date of Patent: Mar. 3, 1987

[54] OPTICAL REFLECTANCE STANDARD FOR GEOLOGICAL EXPLORATION

[75] Inventor: Sheldon E. Sommer, Dallas, Tex.

[73] Assignee: Mobil Oil Corporation, New York, N.Y.

[21] Appl. No.: 575,086

[22] Filed: Jan. 30, 1984

[51] Int. Cl.[4] ............................................. G01N 21/01
[52] U.S. Cl. .................................. 356/243; 250/252.1
[58] Field of Search ...................... 250/252.1; 356/243, 356/418

[56] References Cited

U.S. PATENT DOCUMENTS

| | | | |
|---|---|---|---|
| 3,764,364 | 10/1973 | Seiner | 356/243 X |
| 3,776,642 | 12/1973 | Anson et al. | 356/243 X |
| 4,040,747 | 8/1977 | Webster | 356/243 X |
| 4,047,032 | 9/1977 | Judge et al. | 356/243 X |
| 4,345,840 | 8/1982 | Goetz et al. | 356/418 X |

OTHER PUBLICATIONS

Barringer Research "Ratioing Radiometer, Hand-Held Reflectance Radiometer for the Earch Sciences".
"Optical Characteristics of a Proposed Reflectance Standard" Trytten and Flowers, Applied Optics, Dec. 1965, vol. 5, No. 12.
"Spectral and Bi-Directional Reflectance of Pressed Versus Unpressed Fiberfrax", Applied Optics, vol. 10, No. 7, Jul. 1971.
"Field Standards of Reflectance", Palmer, Photogrametric Engineering and Remote Sensing, vol. 48, No. 10, Oct. 1982, pp. 1623-1625.
"Reflection Properties of Pressed Polytetrafluoroethylene Powder" Weidener and Hsia, J. of the Optical Society of America, vol. 71, No. 7, Jul. 1981.

Primary Examiner—F. L. Evans
Attorney, Agent, or Firm—Alexander J. McKillop; Michael G. Gilman; Charles J. Speciale

[57] ABSTRACT

In geological exploration, an improved optical reflectance includes a coating consisting of micropulverized PTFE powder and cement having similar spectral characteristics to the powder. The coating is bonded to a substrate and the surface of the coating is milled to a matte surface having uniform reflectance characteristics, including Lambertian response.

9 Claims, 9 Drawing Figures

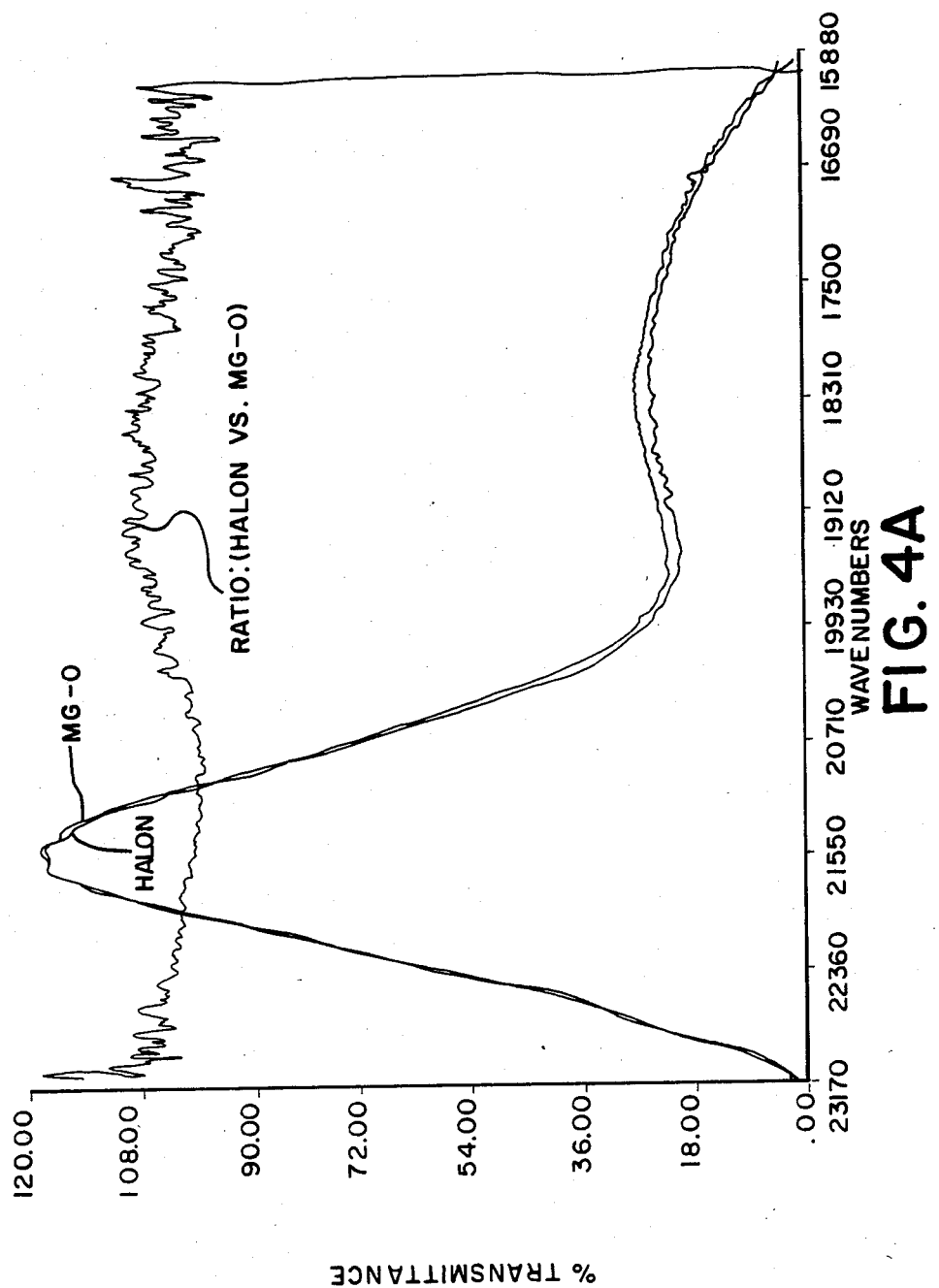

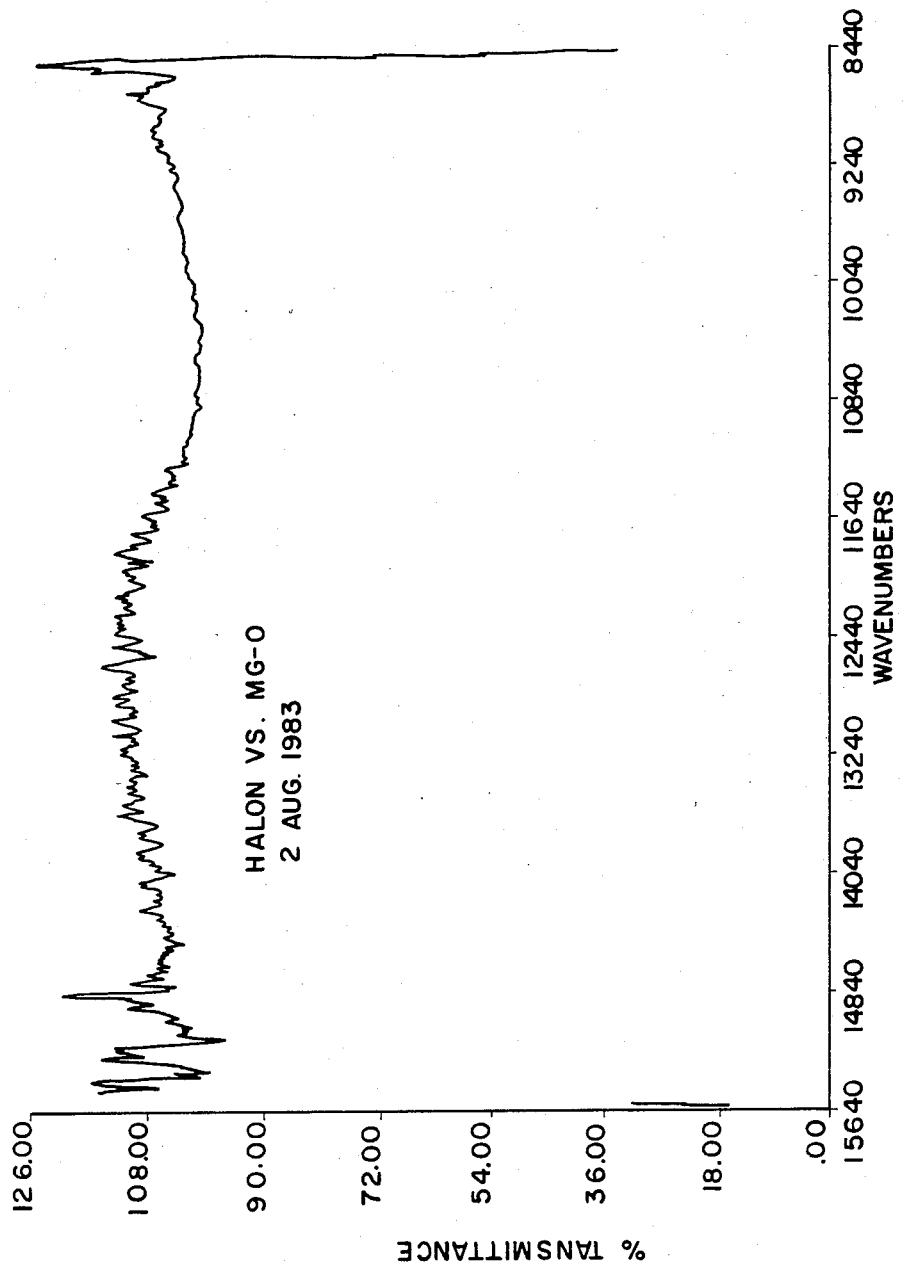

OPTICAL REFLECTANCE STANDARD FOR GEOLOGICAL EXPLORATION

BACKGROUND OF THE INVENTION

This invention relates to the field measurement of mineral, plant, and general surface spectral radiance, and more particularly, to an improved reflectance standard for such measurements.

Radiometers are used in geological exploration to detect outcrops and for geological mapping. Radiometer measurements are used to classify soil, overburden and rocks, and they are used in stratigraphical studies and examination of lithological changes. A typical radiometer used in such studies is the Barringer Research, Ltd. ratioing radiometer described in that company's brochure entitled "BARRINGER RESEARCH RATIOING RADIOMETER, HAND-HELD REFLECTANCE RADIOMETER FOR THE EARTH SCIENCES". In geological exploration, the radiometer is used to detect radiant energy reflected from a target such as the rock being investigated. The detected energy is converted to an electrical signal which is compared to a signal produced by detecting radiant energy from a standard.

Accurate reflectance standards are critical in these investigations. The current practice is to use a material consisting of finely spun filaments of glass in wooly masses of the type commonly used for insulation. More specifically, the Fiberfrax ceramic fiber felt, made by the Carborundum Company, have been extensively used as a reflectance standard. Ihe use of this material is described in "Optical Characteristics of a Proposed Reflectance Standard" Trytten and Flowers, *Applied Optics,* Dec. 1965, Vol. 5, No. 12, and in "Spectral and Bi-Directional Reflectance of Pressed Versus Unpressed Fiberfrax", *Applied Optics,* Vol. 10, No. 7, July 1971.

One of the desirable characteristics of a reflectance standard is that it have a Lambertian surface. That is, the reflectance should be the same regardless of the orientation of the standard with respect to the source of radiation.

Fiberfrax ceramic fiber felt has very good optical characteristics for use as a standard, but it has drawbacks, particularly for field use. This felt does not have a Lambertian surface. For this reason, in field use, Fiberfrax ceramic fiber felt standards must be used with the same orientation between the source of radiation and the standard, and between the standard and the radiometer. Also, it has a crumbling surface which is particularly susceptible to contamination by dirt. The present practice is to periodically scrape off the top layer containing the dirt so that a fresh surface is always presented for reflectance measurements. Because of this, a ceramic fiber felt reflectance standard is commonly used for only a day of field measurements.

Attempts to replace ceramic fiber felt as a reflectance standard for field use have included test cards having surfaces of standard reflectance as described, for example, in "Field Standards of Reflectance", Palmer, *Photogrametric Engineering and Remote Sensing,* Vol. 48, No. 10, Oct. 1982, pp. 1623–1625. These cards do not have a Lambertian surface and they do not have a high efficiency spectral response of the type required for measurements made in geological exploration. For these reasons the cards have not been extensively used in geological exploration.

It is an object of the present invention to provide an improved reflectance standard particularly suitable for field use in geological studies.

It is another object of the present invention to provide a reflectance standard having a Lambertian surface and a surface which is relatively free from dirt contamination.

SUMMARY OF THE INVENTION

In accordance with the present invention, an improved radiant energy reflectance standard consists of a coating of PTFE powder and coating cement having similar spectral characteristics bonded to a substrate. The standard has a Lambertian surface which is particularly resistant to dirt contamination and which can be easily rid of dirt by brushing off small amounts of the material. The standard has good reflectance characteristics for the wavelengths of interest and good efficiency of reflectance characteristics.

The reflectance standard is formed by suspending micropulverized PTFE powder in an air setting refractory coating cement, applying the suspension to a substrate, and drying the suspension to form a coating approximately 1/16" to ¼" thick. The reflectance standard is easily made with very reproducible reflectance characteristics.

The foregoing and other objects, features and advantages of the invention will be better understood from the following more detailed description and appended claims.

SHORT DESCRIPTION OF THE DRAWINGS

FIGS. 4A–4F are spectral response curves for the standard of the present invention and that of the prior art.

DESCRIPTION OF THE PREFERRED EMBODIMENT

Figure 1:
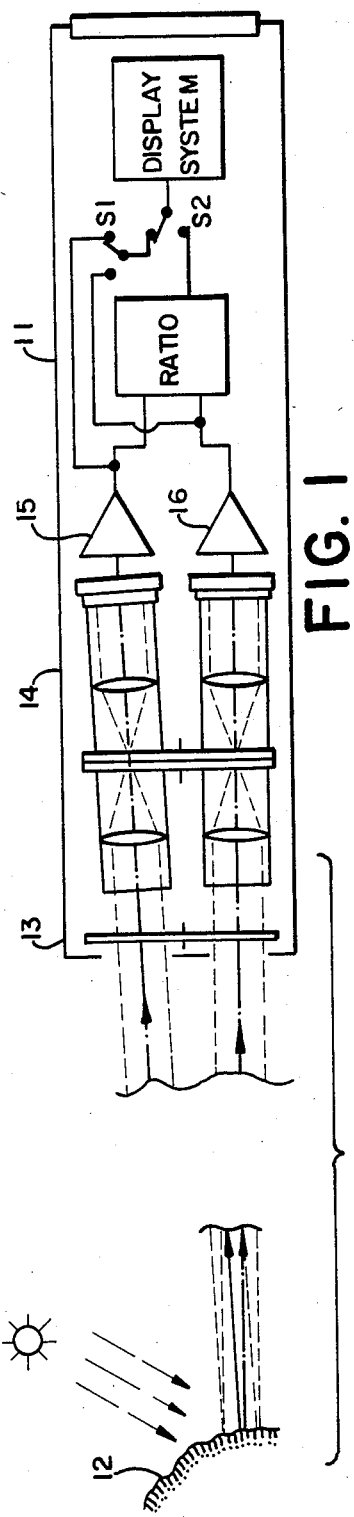
FIG. 1 depicts the use of a radiometer in making target measurements.

Referring to FIG. 1, a radiometer 11 detects radiant energy reflected from a target 12. The radiant energy is detected in two channels through a light chopper 13, an optical train 14, and detectors 15 and 16 which convert the radiant energy to an electrical signal.

Figure 2:
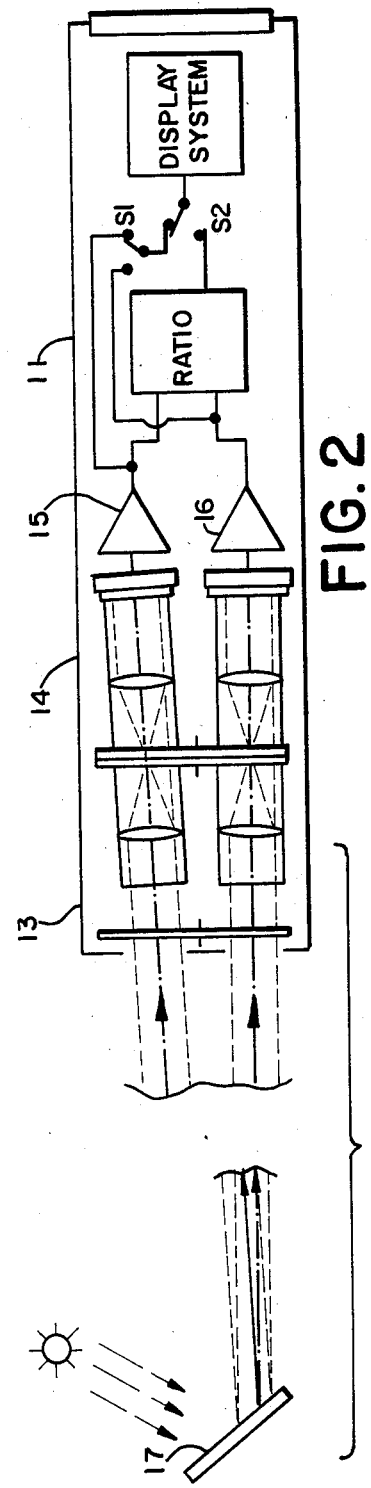
FIG. 2 depicts the same radiometer making standard measurements.

In FIG. 2, the same radiometer is shown detecting radiant energy reflected from a reflectance standard 17. The detected radiant energy reflected from this standard is converted to an electrical signal which is compared to the radiant energy produced from the target to produce a signal which identifies the target by its reflectance characteristics.

Figure 3:
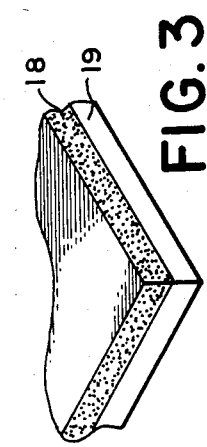
FIG. 3 shows the reflectance standard of the present invention.

FIG. 3 depicts the reflectance standard of the present invention which includes a coating 18 consisting of micropulverized PTFE powder and coating cement bonded to a substrate 19.

Micropulverized PTFE powder has excellent reflection properties which are described in "Reflection of Pressed Polytetrafluoroethylene Powder", Weidener and Hsia, J. of the Optical Society of America, Vol. 71, No. 7, July 1981. This article describes the use of PTFE powder in a light collecting device, an integrating sphere. Such spheres have been used as reflection standards, but not as a standard for a radiometer of the type used to measure radiant energy in geological exploration.

The coating is formed by suspending the PTFE powder in an air setting refractory coating cement. The cement must have spectral characteristics which are similar to that of the PTFE powder. A particularly suitable coating cement is of a type which contains ball milled fibers blended with inorganic additives and sold under the name "Fiberfrax Coating Cement" by Carborundum Company. This bonding cement contains ceramic fibers. If the spectral characteristics are very similar, the resultant coating will have uniform spectral response characteristics. Because of this, it has optical characteristics similar to the Fiberfrax ceramic fiber felt used as reflectance standards as described in the above-mentioned articles. However, to my knowledge, Fiberfrax bonding cement has not been used in optical applications.

The suspension of PTFE powder and coating cement is applied to a substrate such as plexiglass or any suitable rigid surface.

The mixture is air dried and prepared for use by milling it to an even surface.

The spectral response of the resulting surface is comparable to the ceramic fiber felt presently used as a reflectance standard, as evidenced by a comparison of the spectral response tests depicted in FIG. 4. However, the reflectance standard of the present invention is superior in that it has a surface which is not subject to disruption by dirt, wind, or handling. It does not require frequent pressing to achieve a proper surface, nor does it require peeling to remove dirt. Any dirt that lands on the surface is easily removed by brushing the surface lightly with a camels hair type brush. Further, the reflectance standard of the present invention has a Lambertian surface, so the orientation of the standard is not critical.

The reflectance standard of the present invention may be inexpensively prepared in virtually any shape or form for added convenience.

The coating is applied in a thickness of from 1/16" to ¼". The minimum thickness need only be sufficient to provide a good covering of the substrate. The maximum thickness has the constraint that very thick coatings tend to crack and hence, are unacceptable.

EXAMPLES

A matte surface consisting of Halon powder impregnated in a suspension of Fiberfrax QF-180 coating cement was prepared by blending a mixture of 50/50 percent by volume until flowable. Halon is a PTFE powder manufactured by Allied Chemical Co. QF-180 Fiberfrax coating cement is a product of Carborundum Co. The mixture was bonded to pieces of plexiglass approximately 8"×12". The suspension was applied to a thickness of about ¼" and was air dried. The dried mixture was prepared for use by milling it to an even surface. Spectra from this surface are superior to the presently utilized material (Fiberfrax ceramic fiber felt) as shown by the spectral response curves of FIG. 4. These curves compare the spectral response of the standard prepared as above with the response of an MgO standard. This is a precise laboratory standard not suitable for field use. The curves also compare the spectral response of the prior art Fiberfrax ceramic fiber felt with the same MgO standard.

Figure 4B:
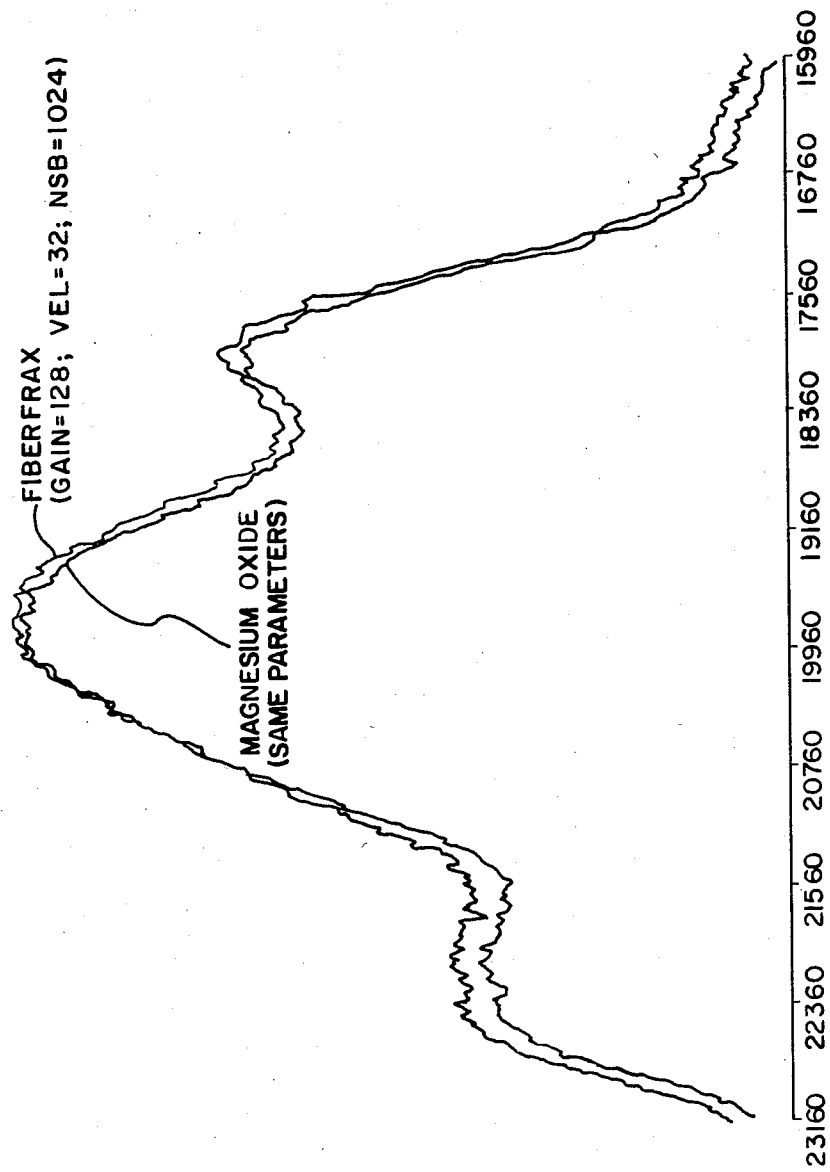

More particularly, FIG. 4A shows percent of transmittance as a function of wave number for the magnesium oxide laboratory standard and the standard prepared with Halon as described above. The third curve in FIG. 4A is the ratio of the other two curves. The ratio is relatively flat, showing a good match between the standard and the present invention for the spectral region under consideration. This spectral region is approximately 0.43 microns to 0.63 microns, ultra violet, blue. (The wave number is the reciprocal of the wave length.) FIG. 4B shows the prior art Fiberfrax ceramic fiber felt compared to the same magnesium oxide laboratory standard over approximately the same spectral region as FIG. 4A. Again, there is a good match between the field standard and the laboratory standard.

Figure 4D:
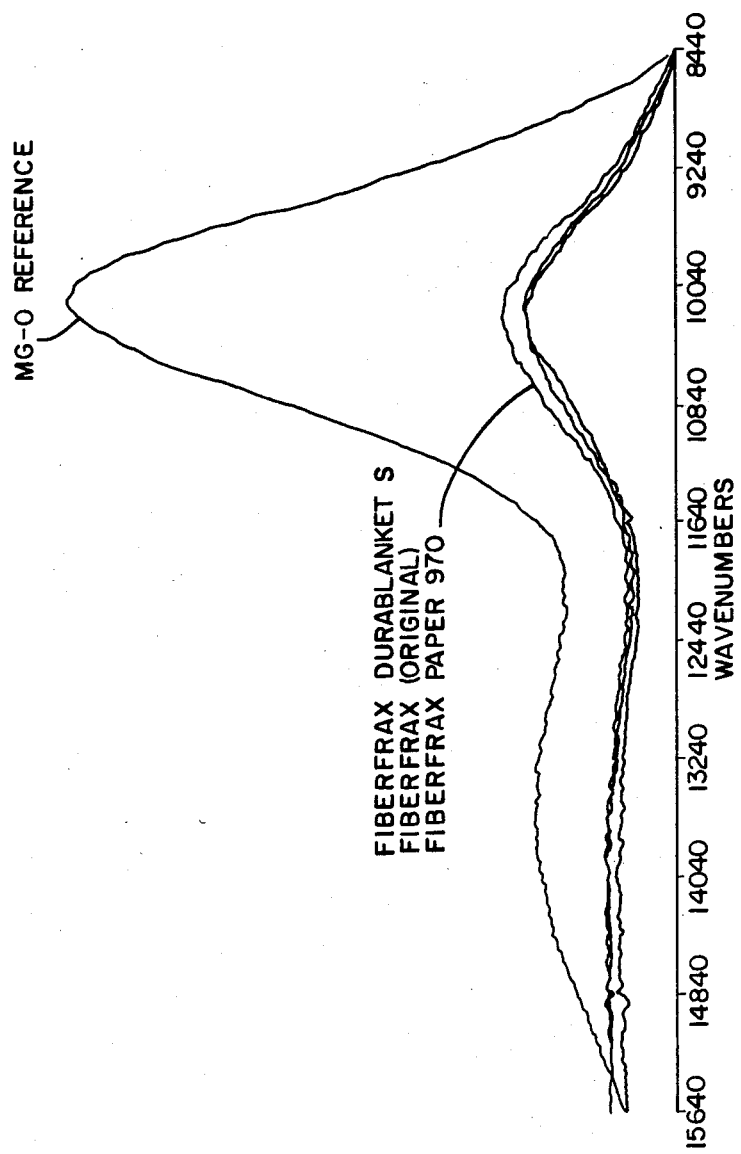

FIG. 4C shows the spectral characteristics of the standard prepared in accordance with the present invention vs. the magnesium oxide laboratory standard over the spectral region of 0.64 microns to approximately 1.2 microns (wave number 15640-8440.) The response of the standard of the present invention is very similar to the magnesium oxide standard. FIG. 4D shows the prior art Fiberfrax ceramic fiber felt compared to the MGO reference over the same spectral region as FIG. 4C. Note that there is a marked departure between the laboratory standard and the Fiberfrax ceramic fiber standard at a wave number of approximately 10040. In this region, the standard of the present invention is better than the prior art.

Figure 4E:
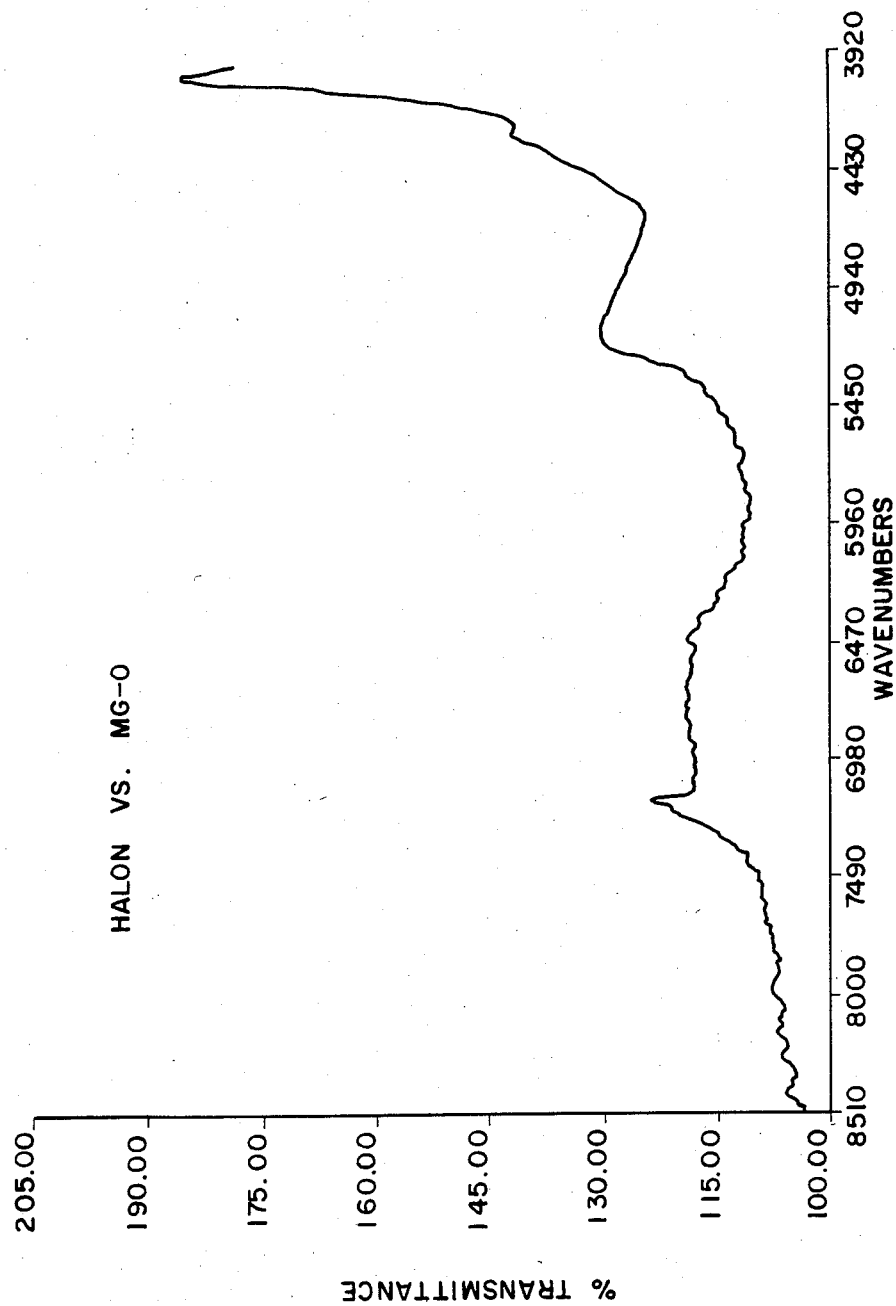
Figure 4F:
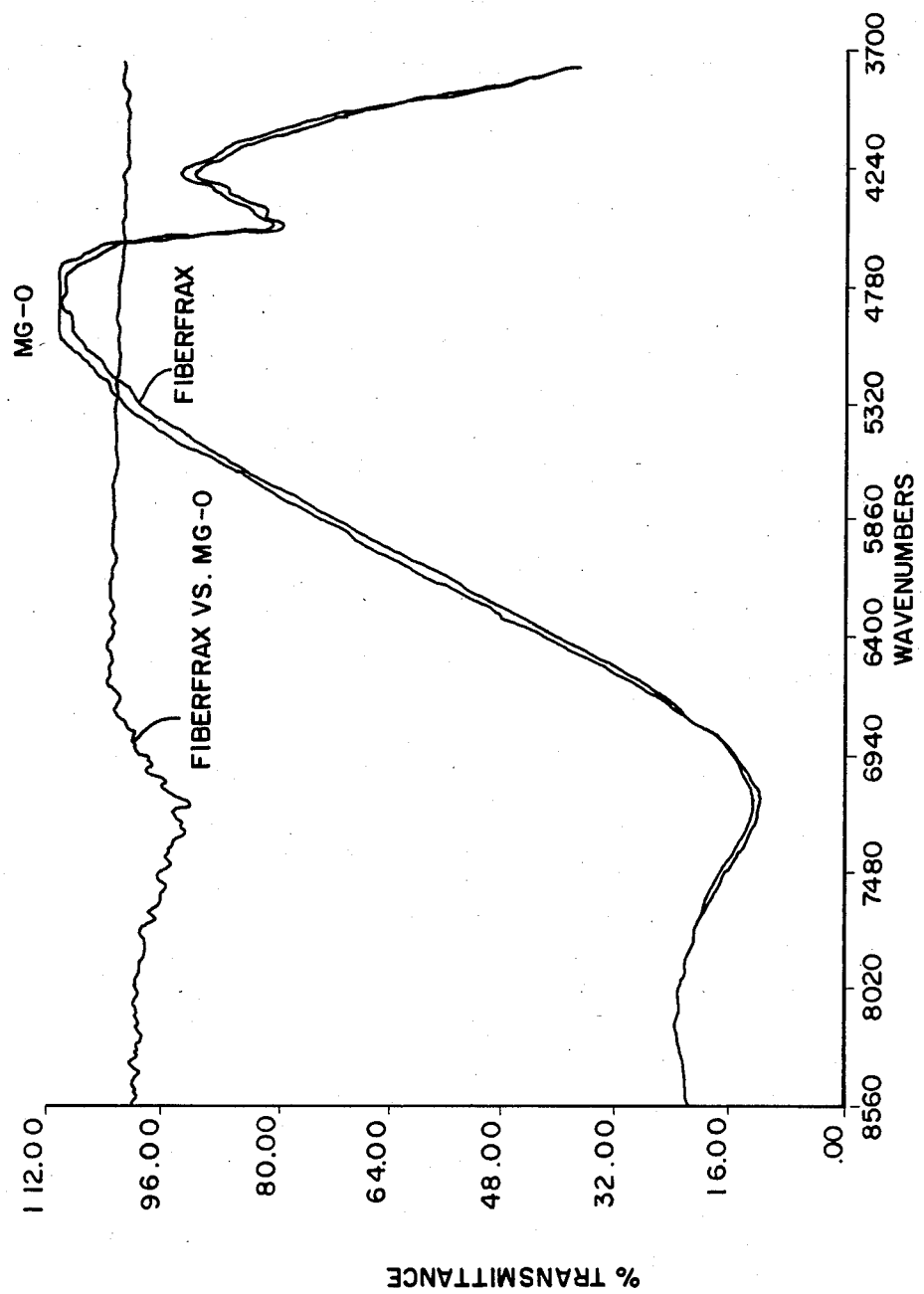

FIGS. 4E and 4F compare the present invention and the prior art to the laboratory standard in the spectral region of approximately 1.16 microns to 2.7 microns, infrared. In this region the standard of the present invention has improved spectral characteristics to the prior art.

In general, good spectral characteristics are exhibited by the present invention and the prior art, but the present invention has other superior characteristics as previously mentioned.

While a particular embodiment of the invention has been shown and described, various modifications are within the true spirit and scope of the invention. The appended claims are, therefore, intended to cover all such modifications.

What is claimed is:

1. In geological exploration wherein radiant energy reflected from a target is detected and converted to an electrical signal which is compared to a signal produced by detecting radiant energy from a standard to identify the geological characteristics of said target, an improved optical reflectance standard comprising:
   a substrate;
   a coating consisting of micropulverized PTFE powder and cement containing ceramic fibres and having similar spectral characteristics to said powder, said coating being bonded to said substrate, said coating having a matte surface having uniform reflectance characteristics.

2. The optical standard recited in claim 1 wherein said surface has a Lambertian response characteristic.

3. The standard recited in claim 1 wherein said coating is between 1/16" and ¼" thick.

4. An improved optical reflectance standard for a radiometer of the type in which radial energy, reflected from a target, is detected and converted to an electrical signal which is compared to a signal produced by detecting radiant energy from a standard, said standard comprising:

a substrate; and a coating consisting of a micropulverized PTFE powder and coating cement bonded to said substrate, said coating cement containing ceramic fibers and having similar spectral characteristics to said powder, said coating having a matte surface having uniform reflectance characteristics.

5. The optical standard recited in claim 4 wherein said surface has a Lambertian response characteristic.

6. The standard recited in claim 4 wherein said coating is between 1/16" and ¼" thick.

7. The method of making an improved optical reflectance standard for a radiometer of the type in which radiant energy is reflected from a target, detected, and converted to an electrical signal which is compared to a signal produced by detecting radiant energy reflected from a standard, said method comprising:

suspending micropulverized PTFE powder in an air-setting refractory coating cement said coating cement containing ceramic fibers having similar spectral characteristics to said powder;

applying the suspension to a substrate; and drying said suspension to form a coating of suspended PTFE powder on said substrate.

8. The method recited in claim 7 further comprising: milling said coating to form a matte surface.

9. The method recited in claim 7 further comprising: forming said coating to a thickness between 1/16" and ¼".

* * * * *